United States Patent [19]

Grimmer et al.

[11] Patent Number: 4,673,742
[45] Date of Patent: Jun. 16, 1987

[54] PREPARATION OF RIBOFLAVIN

[75] Inventors: Johannes Grimmer, Grenaa, Denmark; Hans C. Horn, Lambshein, Fed. Rep. of Germany

[73] Assignee: BASF Aktiengesellschaft, Ludwigshafen, Fed. Rep. of Germany

[21] Appl. No.: 703,523

[22] Filed: Feb. 20, 1985

[30] Foreign Application Priority Data

Feb. 22, 1984 [DE] Fed. Rep. of Germany ....... 3406819

[51] Int. Cl.$^4$ ............................................. C07D 487/02
[52] U.S. Cl. ..................... 544/251; 534/858
[58] Field of Search .......................... 544/251; 534/858

[56] References Cited

U.S. PATENT DOCUMENTS

| 2,343,254 | 3/1944 | Dale | 544/251 |
| 2,847,413 | 8/1958 | Folkers et al. | 544/251 |
| 4,567,261 | 1/1986 | Ernst et al. | 544/251 |
| 4,567,262 | 1/1986 | Grimmer et al. | 544/251 |

FOREIGN PATENT DOCUMENTS 0007737 6/1963 Japan ................................. 544/251

OTHER PUBLICATIONS

Palzelt, et al., Chemical Abstracts, vol. 72, 111780k (1970).
Tishler, et al., J. Am. Chem. Soc., vol. 69, pp. 1487-1492, (1947).
Patzelt, et al., Chemical Abstracts, vol. 70, 68699k (1969) (abstract of Czech. 127,303, 04/15/68).
Gabriel, et al., Chemical Abstracts, vol. 98, 4749x (1983) (abstract of Czech. 195,229, 05/15/82).

Primary Examiner—Donald G. Daus
Assistant Examiner—Diana G. Rivers
Attorney, Agent, or Firm—Oblon, Fisher, Spivak, McClelland & Maier

[57] ABSTRACT

Riboflavin of the formula I

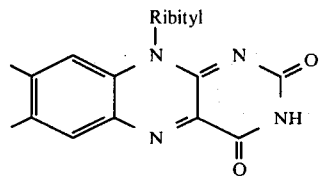

is prepared by condensation of a 4,5-dimethyl-N-(D)-ribityl-2-phenylazoaniline of the formula II

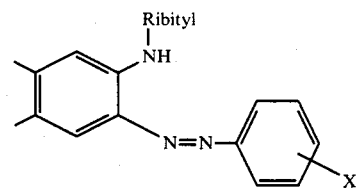

where X is H, —Cl, —NO$_2$ or —CH$_3$ in the o- or p-position, with barbituric acid of the formula III

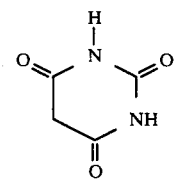

in the presence of an acidic condensing agent in an inert organic solvent by an improved process in which the reaction is carried out in an aliphatic diol or triol derivative of the general formula IV

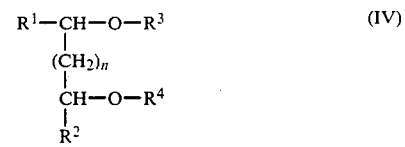

where R$^1$ is H or CH$_3$, R$^2$ is H or CH$_3$— or, when n is 0, is CH$_3$—CO—O—CH$_2$—, R$^3$ is CH$_3$—, C$_2$H$_5$— or CH$_3$—, R$^4$ is CH$_3$—CO—, or is H when R$^3$ is CH$_3$— or C$_2$H$_5$—, and n is 0 or 2, preferably 0, having a boiling point of 80°–180° C., or in a mixture of these as a solvent. In this process, the riboflavin is obtained in particularly pure form and in very good yields.

5 Claims, No Drawings

PREPARATION OF RIBOFLAVIN

The present invention relates to an improved process for the preparation of riboflavin (I; vitamin $B_2$) by condensation of a 4,5-dimethyl-N-(D)-ribityl-2-phenylazoaniline (II) with barbituric acid (III) in the presence of an acidic condensing agent in an organic solvent.

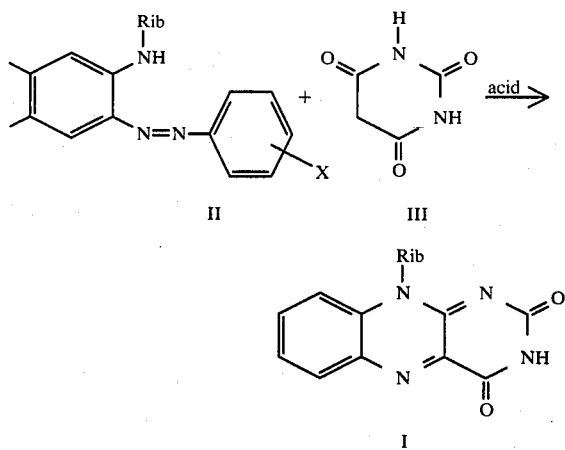

Rib = ribityl
X = H or a p— or o-substituent, such as —Cl, —$NO_2$ or —$CH_3$.

Apart from the improvement according to the invention, this last step in the riboflavin synthesis has been disclosed in a number of publications. The reaction of II with III to give I was first described in J. Am. Chem. Soc. 69 (1947), page 1487 et seq. The reaction medium particularly stated in this publication is a mixture of glacial acetic acid and dioxane. Since large amounts of the relatively expensive solvent dioxane have to be used in this process and, furthermore, dioxane is unacceptable because it is hazardous to health, this process is unsuitable for the preparation of riboflavin on an industrial scale.

A detailed investigation into the suitability of various organic acids as catalysts for the reaction of II with III has been described by Berezowski et al. in J. Gen. Chem. USSR 31 (1961), page 3444 et seq. Boiling butanol was used as the solvent. The maximum yield of about 70% obtained in this process is unsatisfactory for an industrial-scale process, especially when it is obtained in the final reaction step of a multi-stage process, and since these yields were furthermore obtained only when a fairly large excess of III was used.

According to Czechoslovak Pat. No. 127,303, II is reacted with III in the presence of glacial acetic acid in butanol or dioxane. The yields obtained are no higher than 78%.

Japanese Preliminary Published Application 7737/1963 discloses the reaction of II with III in a mixture of alkanols having a boiling point of from 80° to 120° C. and glacial acetic acid over $Al_2O_3$ or purified diatomaceous earth. The yields are 67–69% of theory.

A disadvantage of reacting II with III in an alkanol is that partial esterification of the alkanol with the acetic acid takes place as a side reaction, with the result that, on the one hand, water over and above the water of condensation resulting from the reaction enters the reaction mixture and interferes with the further condensation of II with III, and, on the other hand, the solvent has to be regenerated by an expensive procedure. Furthermore, the physical properties of the solvent/catalyst system and the reaction and crystallization conditions in the synthesis result in a less pure riboflavin.

Furthermore, Japanese Preliminary Published Application 10151 discloses a process for the condensation of II with III in a mixture of a solvent, such as ethyl acetate, and nitrobenzene or a nitroalkane. The yields are 82–84%. The disadvantages of this process are that the space-time yields are too low and it is necessary for nitrobenzene and the like to be present, this compound having a very high vapor pressure and being extremely poisonous.

Czechoslovak Pat. No. 195,229 discloses a process for the preparation of I from II and III in a mixture of xylene, a $C_3$—$C_5$—alkanol, glacial acetic acid and acetates. The yields are 86–87.4% of a relatively pure compound I. The disadvantages of this process are the expensive working-up procedure for the solvent mixture used, poor space-time yields and difficulties in filtering off the product, since I is precipitated from this mixture in the form of relatively small crystals which are difficult to filter.

Furthermore, Japanese Preliminary Published Application 3575/1957 discloses a process for the preparation of I by reacting II with III in a mixture of an organic solvent and glacial acetic acid over an acidic salt, such as $SnCl_2$, $ZnCl_2$, $FeCl_2$, $AlCl_3$ or $BiCl_3$ as a catalyst. I is obtained in yields greater than 80% of theory. The disadvantages of this process are that the good yields mentioned are obtained only if barbituric acid is used in an excess of from 75 to 110%, and that the resulting riboflavin must in each case be subjected to subsequent purification associated with loss of yield, and the regeneration of the solvents and of the metal salts is very time-consuming and expensive.

It is an object of the present invention to provide a solvent in which the acid-catalyzed condensation of II and III takes place with good yields and good space-time yields, from which, furthermore, I crystallizes out in very high purity, and which can also be reused very often and/or regenerated in a very simple manner.

We have found that this object is achieved, and that, surprisingly, the disadvantages of the prior art are substantially overcome when certain aliphatic diol or triol derivatives are used as solvents, and I is obtained in very good yields and in very pure crystalline form.

The present invention therefore relates to an improved process for the preparation of riboflavin of the formula I

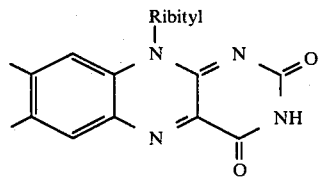

by condensation of a 4,5-dimethyl-N-(D)-ribityl-2-phenylazoaniline of the formula II

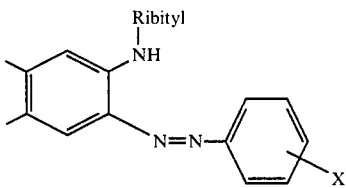

where X is H, —Cl, —NO$_2$ or —CH$_3$ in the o— or p-position, with barbituric acid of the formula III

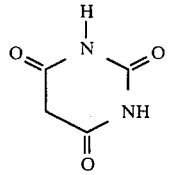

in the presence of an acidic condensing agent in an organic solvent, wherein the reaction is carried out in an aliphatic diol or triol derivative of the general formula IV

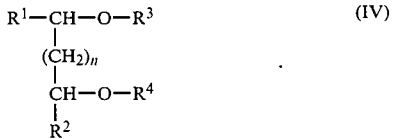

where R$_1$ is H or CH$_3$, R$^2$ is H or CH$_3$— or, when n is 0, is CH$_3$—CO—O—CH$_2$—, R$^3$ is CH$_3$—, C$_2$H$_5$— or CH$_3$—CO—, R$^4$ is CH$_3$—CO—, or is H when R$^3$ is CH$_3$— or C$_2$H$_5$—, and n is 0 or 2, preferably 0, having a boiling point of 80°–180° C., or in a mixture of these as a solvent.

In a particularly advantageous embodiment of the process, the reaction is carried out in ethylene glycol diacetate or 1-methoxypropan-2-ol, or in a mixture of these.

When the solvents according to the invention are used, virtually quantitative yields of I are obtained. The purity of I is never less than 94%, and is generally greater than 95%.

It is surprising that high yields and purities are also achieved in the formation of riboflavin when an alkoxyalkanol, such as 1-methoxypropan-2-ol, is used as a solvent for the reaction. We have found that a mixture of, for example, methoxypropanol and glacial acetic acid, ®Versatic acid, propionic acid or pivalic acid shows scarcely any tendency to undergo esterification in the course of this reaction, so that only small amounts of solvent and acid are lost, and expensive regeneration is therefore not required.

The improvement in the purity to greater than 96% when a mixture of the novel acetates, alkoxyalkanol acetates or alkoxyalkanols is used in the presence of acidic catalysts is completely unexpected.

The starting compounds II and their preparation are known. In general, the cheapest compound of this series, ie. the phenylazo derivative, is used. In principle, however, compounds in which the ortho-position or, in particular, the para-position of the azophenyl group carries substituents such as methyl, chlorine or nitro are also suitable. The starting compounds need not be specially purified, but can also be used in the form of crude products. The yields in this case are based on II present in the starting material.

According to the invention, particularly suitable inert organic solvents or diluents of the general formula IV are the acetates of polyhydric aliphatic alcohols, such as ethylene glycol diacetate, butane-1,4-diol diacetate or glycerol triacetate, alkoxyalkanol acetates, such as 2-ethoxyethanolacetate (which may also be called 2-ethoxyethyl acetate), and even alkoxyalkanols, such as 1-methoxypropan-2-ol. Ethylene glycol diacetate or 1-methoxypropan-2-ol or a mixture of these is very particularly advantageously used. The amount of solvent is in general about 2–12 liters per kg of II.

Suitable acidic condensing agents are in principle all acids described to date in the literature for this reaction, preferably weak organic acids, such as glacial acetic acid, propionic acid, phenylacetic acid, benzoic acid, trimethylacetic acid (pivalic acid), 2,2-dimethylbutanoic acid, 2,2-dimethylpentanoic acid and 1-methylcyclopentanecarboxylic acid.

Of particular importance industrially are the especially cheap glacial acetic acid and commercially available mixtures of synthetic acids which essentially contain saturated tertiary carboxylic acids, especially Versatic ®-10-acid, a synthetic C$_{10}$-carboxylic acid from Shell Chemie, and similar products from Esso, which are available commercially under the name neo-acids. Examples of these are neopentanoic acid, which contains trimethylacetic acid as the principal component, and neodecanoic acid, whose composition is probably similar to that of Versatic-10-acid.

The amount of the carboxylic acid is preferably from 0.5 to 6 moles per mole of II; for example, this corresponds to about 0.83-1 kg per kg of II in the case of glacial acetic acid, and to 2.36–2.85 kg per kg of II in the case of Versatic-10-acid.

A particular advantage of the novel process is that substantially higher yields than those achieved to date are obtained even when equimolar amounts of II and III are used. These yields are about 85%, but can be increased further to well above 90% if III is used in an excess of up to 0.3 mole. Larger excesses do not have an adverse effect but do not result in any noticeable increase in yield.

The reaction temperatures are 80°–120° C., but the reaction is preferably carried out at above 100° C., ie. at about 100°–115° C. and in an appropriately high-boiling solvent. At 100° C., the reaction time is about 5–15 hours.

With the aid of the novel process, riboflavin is obtained from II and III in an advantageous manner, in very pure form and in very good yields.

EXAMPLES 1 TO 9

A mixture of 40 g of 4,5-dimethyl-N-(D)-ribityl-2-phenylazoaniline (87% strength with respect to the required 2-phenylazo isomer; corresponding to 0.0966 mole), 16 g (0.125 mole) of barbituric acid and the amounts of acids and solvents shown in the Table below was heated at the stated reaction temperature for the stated reaction time. The reaction mixture was then cooled to 60° C., and the precipitate which separated out was filtered off under suction, washed with methanol, then with water at 60° C. and again with methanol, and dried in a drying oven at 80°–90° C. The yields and purities obtained are shown in the Table. The percentage yields are based on 100% pure 4,5-dimethyl-N-(D)- ribityl-2-phenylazoaniline employed and 100% pure riboflavin.

TABLE

| Example | Solvent | [ml] | Acid [ml] | Reaction time [h] | Temp. [°C.] | Yield [g] | Purity [%] | Yield [% of theory] |
|---|---|---|---|---|---|---|---|---|
| 1 | CH₂—O—Ac<br>\|<br>CH₂—O—Ac | 200 | glacial acetic acid 20 | 10 | 110–15 | 35.9 | 95.1 | 93.9 |
| 2 | CH₂—O—C₂H₅<br>\|<br>CH₂—O—Ac | 180 | glacial acetic acid 30 | 10 | 115 | 34.9 | 94.4 | 90.5 |
| 3 | CH₂—O—CH₃<br>\|<br>CH—OH<br>\|<br>CH₃ | 200 | glacial acetic acid 20 | 10 | 110 | 32.8 | 96.1 | 86.6 |
| 4 | CH₂—O—CH₃<br>\|<br>CH—OH<br>\|<br>CH₃ | 120 | Versatic-10-acid 98 | 10 | 110–20 | 35.4 | 95 | 92.4 |
| 5 | CH₂—O—Ac<br>\|<br>CH—O—Ac<br>\|<br>CH₂—O—Ac | 200 | glacial acetic acid 20 | 3 | 120 | 32.9 | 94.9 | 85.9 |
| 6 | CH₂—O—Ac   CH₂—O—CH₃<br>\|                  \|<br>CH₂—O—Ac + CH—OH<br>                    \|<br>                    CH₃<br>100 ml | 100 | glacial acetic acid 10 | 10 | 120 | 34.1 | 95.2 | 89.2 |
| 7 | CH₂—O—Ac   CH₂—O—CH₃<br>\|                  \|<br>CH₂—O—Ac + CH—OH<br>                    \|<br>                    CH₃<br>170 ml | 30 | glacial acetic acid 10 | 10 | 120 | 35.8 | 96.8 | 95.3 |
| 8 | CH₂—OCH₃<br>\|<br>CH—OH<br>\|<br>CH₃ | 200 | propionic acid 20 | 10 | 110–15 | 32.7 | 96.3 | 86.6 |
| 9 | CH₂—O—Ac<br>\|<br>(CH₂)₂<br>\|<br>CH₂—O—Ac | 200 | glacial acetic acid 20 | 10 | 110–15 | 34.1 | 94.0 | 88.3 |

We claim:
1. An improved process for the preparation of riboflavin of formula I:

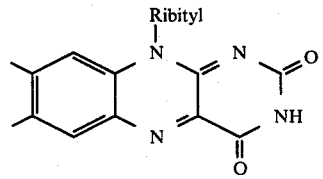

comprising:
condensing a 4,5-dimethyl-N-(D)-ribityl-2-phenylazoaniline of formula II:

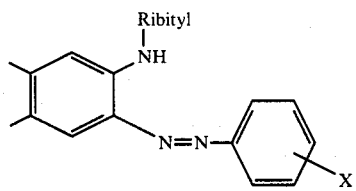

wherein X is H, Cl, NO₂ or CH₃ in the o— or p-position, with barbituric acid of formula III:

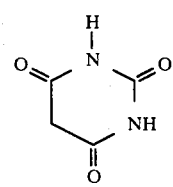

in the presence of an acidic condensing agent in an organic solvent selected from the group consisting of ethylene glycol diacetate, butan-1,4-diol diacetate, glycerol triacetate, 1-methoxypropan-2-ol and ethoxy ethanol acetate or a mixture of these derivatives.

2. The process as claimed in claim 1, wherein said solvent is ethylene glycol diacetate, or a solvent mixture containing ethylene glycol diacetate ingredient as a component.

3. The process as claimed in claim 1, wherein said solvent is 1-methoxypropan-2-ol or a mixture of solvent ingredients containing 1-methoxypropan-2-ol.

4. The process as claimed in claim 1, wherein said reaction is conducted at a temperature ranging from 80°–120° C.

5. The process as claimed in claim 1, wherein said acetate of a polyhydric aliphatic alcohol is ethylene glycol diacetate, butane-1,4-diol diacetate or glycerol triacetate.

* * * * *

UNITED STATES PATENT AND TRADEMARK OFFICE
CERTIFICATE OF CORRECTION

PATENT NO. : 4,673,742

DATED : June 16, 1987

INVENTOR(S) : Johannes Grimmer, et al

It is certified that error appears in the above-identified patent and that said Letters Patent is hereby corrected as shown below:

The Foreign Application Priority Data is printed incorrectly on the Letters Patent.
Should read as follows:

-- Feb. 22, 1984  [DE]  Fed. Rep. of Germany ...... 3406319 --

Signed and Sealed this

Twenty-ninth Day of September, 1987

Attest:

DONALD J. QUIGG

*Attesting Officer*  *Commissioner of Patents and Trademarks*